US009000217B2

(12) United States Patent
King

(10) Patent No.: US 9,000,217 B2
(45) Date of Patent: Apr. 7, 2015

(54) TRANSAMINATION OF NITROGEN-CONTAINING COMPOUNDS TO HIGH MOLECULAR WEIGHT POLYALKYLENEAMINES

(75) Inventor: Stephen W. King, League City, TX (US)

(73) Assignee: DOW Global Technologies LLC, Midland, MI (US)

( * ) Notice: Subject to any disclaimer, the term of this patent is extended or adjusted under 35 U.S.C. 154(b) by 0 days.

(21) Appl. No.: 13/884,477

(22) PCT Filed: Oct. 20, 2011

(86) PCT No.: PCT/US2011/057047
§ 371 (c)(1),
(2), (4) Date: May 9, 2013

(87) PCT Pub. No.: WO2012/064484
PCT Pub. Date: May 18, 2012

(65) Prior Publication Data
US 2013/0225864 A1  Aug. 29, 2013

Related U.S. Application Data

(60) Provisional application No. 61/412,029, filed on Nov. 10, 2010.

(51) Int. Cl.
*C07C 209/60* (2006.01)
*C07C 209/54* (2006.01)
*C07C 209/64* (2006.01)

(52) U.S. Cl.
CPC ............. *C07C 209/54* (2013.01); *C07C 209/64* (2013.01)

(58) Field of Classification Search
CPC ........................... C07C 209/54; C07C 209/60

USPC .................................................. 564/470, 512
See application file for complete search history.

(56) References Cited

U.S. PATENT DOCUMENTS

| 4,568,746 A | 2/1986 | Cowherd, III |
| 6,465,601 B1 | 10/2002 | Wiesendanger et al. |
| 6,534,441 B1 | 3/2003 | Bartley et al. |
| 7,053,247 B2 | 5/2006 | Li et al. |
| 2005/0095189 A1 | 5/2005 | Brey et al. |
| 2008/0132725 A1 | 6/2008 | Melder et al. |
| 2009/0018040 A1 | 1/2009 | Eveland et al. |
| 2010/0087681 A1 | 4/2010 | Petraitis et al. |
| 2010/0087682 A1 | 4/2010 | King et al. |
| 2010/0087683 A1 | 4/2010 | Cook et al. |
| 2010/0087684 A1 | 4/2010 | Do et al. |
| 2010/0094007 A1 | 4/2010 | King et al. |
| 2010/0094008 A1 | 4/2010 | King et al. |
| 2010/0137642 A1 | 6/2010 | King et al. |

FOREIGN PATENT DOCUMENTS

| EP | 0308893 | 3/1989 |
| EP | 0308894 | 3/1989 |
| GB | 1 508 460 | 4/1978 |
| GB | 1 551 127 | 8/1979 |
| JP | 60-239442 | 11/1985 |
| WO | WO 92/17437 | 10/1992 |

*Primary Examiner* — Brian J Davis
(74) *Attorney, Agent, or Firm* — Kagan Binder, PLLC

(57) ABSTRACT

A process for preparing high molecular weight acyclic polyamines comprising providing a reaction mixture that includes at least a first component comprising a first organic, nitrogen-containing compound that contains at least two non-tertiary amine groups separated from one another by a ternary or higher carbon atom spacing that can be transaminated in the presence of a hydrogenation/dehydrogenation catalyst to form a mixture of higher molecular weight, acyclic polyamines while minimizing the formation of cyclic polyamines.

13 Claims, No Drawings

US 9,000,217 B2

TRANSAMINATION OF NITROGEN-CONTAINING COMPOUNDS TO HIGH MOLECULAR WEIGHT POLYALKYLENEAMINES

This application claims the benefit from International No. PCT/US2011/057047, which was granted an International Filing date of Oct. 20, 2011, which in turn claims the benefit of U.S. Provisional Patent Application Ser. No. 61/412,029, filed Nov. 10, 2010, entitled TRANSAMINATION OF NITROGEN-CONTAINING COMPOUNDS TO HIGH MOLECULAR WEIGHT POLYALKYLENEAMINES, which applications are incorporated herein by reference in their entireties.

FIELD OF THE INVENTION

The present invention relates to processes that use transamination to prepare high molecular weight, predominately acyclic amine product mixtures from reactants comprising nitrogen-containing starting compounds. The molar content of the starting compounds can be adjusted to customize the product composition for desired end uses.

BACKGROUND OF THE INVENTION

Transamination techniques can be used to prepare amine compounds and mixtures of amine compounds from lower molecular weight amines. Transamination can provide acyclic and/or cyclic amine products.

GB Patent No. 1508460 discloses the transamination of ethylenediamine (EDA). U.S. Pat. Nos. 4,568,746 and 7,053,247 also discloses the transamination of EDA. GB Patent No. 155127 discloses the transamination of 1,3-diaminopropane (1,3-DAP). U.S. Pat. No. 6,465,601 discloses the preparation of mixed amines by the transamination of a substituted phenolic compound (Mannish base) with another amine. The mixed amines are useful as accelerators for curable epoxy and polyurethane systems. US 2008/0132725 A1 discloses the preparation of bis(3-aminopropyl)amine (dipropylenetriamine, DPTA) by the continuous reaction of 1,3-propylenediamine in the presence of a heterogeneous catalyst in a reaction column. None of these publications disclose the preparation of higher molecular weight polyamines. In fact, they generally teach processes wherein such materials are not made or if made can be redecomposed to the dimers and trimers under the reaction conditions employed.

Although transamination has proved itself as a viable way to manufacture amines on an industrial scale, several challenges remain. First, the ability to customize product mixtures for desired end uses can be limited. Additionally, some processes produce mixtures whose contents promote the formation of cyclic polyamines and discourage the formation of higher molecular weight, acyclic polyamines. While cyclic species are desired for some applications, higher molecular weight, acyclic species are also desired for many other applications. For example, higher molecular weight, acyclic linear species are useful in a variety of applications such as paper manufacture, water treatment conditioning, plating, bath agents, dispersing agents, asphalt additives, corrosion inhibitors, epoxy curing agents, fuel and lubricant additives, mineral processing aids, wood treating, etc. While there are a number of processes that form higher molecular weight polyamines, they generally form only a small quantity of these amines and/or produce undesirable byproducts. It would be desirable to have a process that could minimize the formation of cyclic amines and encourage the formation of higher molecular weight amines from readily available starting materials.

U.S. Patent Publication 2009/0018040 discloses that higher molecular weight polyamines are desirable for some purposes. It describes a method for forming higher molecular weight polyethyleneamines in which lower molecular weight ethyleneamines are coupled through the use of difunctional linking groups such as epihalohydrins, maleates, α-halogenated acids, and malonates. The use of such linking groups to build molecular weight is not cost effective and can introduce other functional groups, which are not desired.

Higher molecular weight polyamines, such as higher molecular weight ethyleneamines (i.e., amines containing 4 or more N atoms) may be produced from ethylene dichloride and ammonia. This process, sometimes referred to as the EDC process, produces a complex mixture of various linear, cyclic, and branched products with a number-average molecular weight of 250-300 g/mole. This process produces a significant amount of cyclic and branched amines.

SUMMARY OF THE INVENTION

The present invention provides improved strategies for using transamination techniques to prepare higher molecular weight, acyclic polyamine product mixtures. Such higher molecular weight, acyclic polyamine product mixtures are mixtures of acyclic, preferably linear, polyamines that contain only small amounts, if any, of cyclic amines.

The present invention is based in part upon using reaction mixtures for transamination that include a first component that comprises at least a first organic, nitrogen-containing compound that contains at least two non-tertiary amine groups separated from one another by a ternary or higher carbon atom spacing, and that can be transaminated to form a mixture of higher molecular weight, acyclic polyamines while minimizing the formation of cyclic polyamines. Optionally, a second component comprising a second nitrogen-containing compound may also be employed in the reaction mixture. The optional second component contains at least two nitrogen-containing groups separated from one another by a second carbon atom spacing. The second carbon atom spacing may the same as or different from the carbon atom spacing of the first component. Examples of useful second nitrogen-containing compounds include dinitriles, aminonitriles, and polyamines.

As used herein, the term polyamine refers to a compound that includes at least two amine groups. With respect to a nitrogen-containing compound that comprises a polyamine, at least two amine groups of the compound are non-tertiary. Thus, at least two amine groups of a polyamine reactant can be primary, secondary, or a combination thereof. As long as a polyamine compound includes at least two non-tertiary amine groups, the compound optionally may also include tertiary amine group(s) as well.

As used herein, the term "carbon atom spacing" refers to the number of carbon atoms between the nitrogen-containing functional groups of the first and optional second components. For example, the term ternary spacing refers to the backbone or portion thereof that separates the nitrogen-containing groups, e.g., amine or other nitrogen-containing groups, of the first and second components by a backbone spacing of three carbon atoms, and the term quaternary spacing means refers to nitrogen-containing groups separated by a backbone spacing of four carbon atoms.

As used herein, the term high molecular weight refers to the molecular weight of a polyamine product(s) resulting from the practice of the present invention. These polyamines typically comprise 4 or more N atoms, although as few as three N atoms are possible in the context of the present invention. Thus, high molecular weight includes a molecular weight average of at least about 130, preferably at least about 180. The upper limit of the molecular weight average is not critical to the invention. In an aspect of the invention, the upper limit of the molecular weight average is about 1000, preferably about 800.

As used herein, the term acyclic refers to a polyamine that is a linear, a branched, or a mixture of a linear and branched polyamine compound. The polyamine mixture(s) resulting from the present invention may contain a minor amount, i.e., less than about 1 weight percent, of a cyclic polyamine.

In contrast to the polyamine reactants, the polyamine products made using methods of the present invention may include two or more primary, secondary, and/or tertiary amine groups, or combinations thereof. Preferred polyamine reactants are primary diamines.

The nature of the product composition can be easily customized for desired end uses simply by adjusting the molar content of the nitrogen-containing compounds in the reaction mixture. The molar content can be selected to favor product mixtures that include essentially no cyclic polyamine materials, that is less than 1 weight % cyclic polyamine.

The practice of the invention can be used to prepare compositions containing novel acyclic congener products of triamines, tetramines, or other polyamines. As used herein, congeners of polyamine products are variants, or different configurations of the polyamine product(s), that contain the same number of N atoms.

The methodology of the invention provides the production of predominately mixed acyclic polyamines useful for a variety of end-use applications and offers much better control over the resultant higher molecular weight, and acyclic/cyclic ratio of the product composition when more than one reactant is used.

In one aspect, the present invention provides a method of making a linear high molecular weight polyamine-containing product mixture comprising the steps of:
  (a) providing a reaction composition comprising one or more nitrogen-containing compounds comprising a first, component that has at least two non-tertiary amine groups separated from one another by at least a ternary or higher carbon atom spacing (C3 or greater spacing) and, optionally, a second component that has at least two nitrogen containing groups separated from one another by a second carbon atom spacing; and
  (b) subjecting the reaction composition to a transamination reaction in the presence of a hydrogenation/dehydrogenation catalyst to obtain the linear high molecular weight polyamine-containing mixture.

In another aspect, the present invention provides a method of making an acyclic polyamine product mixture comprising the steps of:
  (a) providing a reaction composition comprising a first component comprising at least a first nitrogen-containing compound having at least two non-tertiary amine groups separated from one another by a ternary or greater carbon atom spacing (C3 spacing) and a second component comprising a nitrogen-containing compound having (i) at least two non-tertiary amine groups separated from one another by a ternary or greater carbon atom spacing (C3 or greater spacing), (ii) at least two nitrile functionalities separated by at least one carbon atom (C1 spacing), (iii) at least one nitrile functionality and one non-tertiary amine functionality separated from one another by a binary or greater carbon atom spacing (C2 or greater spacing), or (iv) combinations thereof; and
  (b) subjecting the reaction composition to a transamination reaction in the presence of a hydrogenation/dehydrogenation catalyst to obtain the acyclic polyamine mixture.

In another aspect of the present invention relates to a method of making a high molecular weight mixture of polyamine congeners comprising the steps of combining first and second nitrogen-containing components as described above and subjecting the first and second nitrogen-containing components to a transamination reaction in the presence of a hydrogenation/dehydrogenation catalyst to obtain a product mixture comprising the mixture of polyamine congeners.

In another aspect of the invention, the first component is a polyamine that may be represented by the formula

FORMULA I

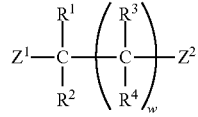

wherein $Z^1$ and $Z^2$ are independently primary or secondary amines;
$R^1$, $R^2$, $R^3$, and $R^4$ are, independently H or substituted or unsubstituted hydrocarbyl, and
w is an integer of 2 or more, preferably from 2 to about 10, more preferably from about 2 to about 5.

In another aspect of the invention, the second nitrogen-containing compound comprises a nitrile-containing compound having the formula

FORMULA II

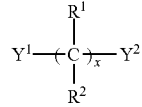

wherein $Y^1$ and $Y^2$ are each CN wherein x is an integer of from 1 to about 10, preferably from 1 to about 5; most preferably 1;
or $Y^1$ is CN and $Y^2$ is independently a non-tertiary amine wherein x is an integer of from 2 to about 10, preferably from 2 to about 5; most preferably 2; and
$R^1$ and $R^2$ are independently H or substituted or unsubstituted hydrocarbyl.

In another aspect, the present invention relates to a method of making an acyclic polyamine mixture, comprising the steps of: providing information indicative of a transamination product mixture composition as a function of a molar content of a first component that has at least two non-tertiary amine groups separated from one another by at least a ternary or higher carbon atom spacing (C3 or greater spacing) and a second component that has at least two nitrogen containing groups separated from one another by a second carbon atom spacing; using the information to provide a reaction mixture comprising the first and second components; and subjecting the reaction mixture to a transamination reaction in the presence of a hydrogenation/dehydrogenation catalyst.

In another aspect, the present invention relates to a method of making an amine mixture, comprising the steps of: providing a reaction mixture comprising a first and second components as described above, wherein the molar content of the first component comprises at least about 90%, preferably 95%, of the reaction mixture; and subjecting the reaction mixture to a transamination reaction in the presence of a hydrogenation/dehydrogenation catalyst.

In another aspect, the present invention relates to a mixture of polyamines obtained by the method(s) of the invention.

DETAILED DESCRIPTION OF PRESENTLY PREFERRED EMBODIMENTS

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods; materials, and compositions described.

All publications and patents mentioned herein are incorporated herein by reference in their respective entireties for the purpose of describing and disclosing, for example, the constructs and methodologies that are described in the publications which might be used in connection with the presently described invention.

Unless defined otherwise herein, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

The present invention provides strategies for making useful acyclic polyamine mixtures by methodologies that comprise subjecting a first component that has at least two non-tertiary amine groups that are separated from one another by a ternary or greater carbon spacing (C3 or greater spacing). Optionally, a second component comprising a nitrogen-containing compound may also be present in the reaction.

Examples of first components useful in the invention may be represented by FORMULA I.

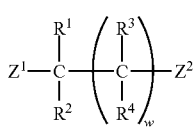

FORMULA I wherein $Z^1$ and $Z^2$ are independently primary or secondary amines;

R1, $R^2$, $R^3$ and $R^4$ are as defined above; and w is an integer of 2 or more, preferably from 2 to about 10, more preferably from about 2 to about 5.

Hydrocarbyl groups that may be used in the various components described herein include linear, branched, or cyclic hydrocarbyl such as alkyl, aryl, aralkyl, or the like; a monovalent moiety including one or more heteroatoms; polyether chains comprising one or more oxyalkylene repeating units such as —$R^5$O—, wherein $R^5$ is often alkylene of 2 to 5 carbon atoms; other oligomeric or polymer chains of at least 2 repeating units; —$R^6NR^1R^{2'}$ wherein R1 and R2 are as described above, and $R^6$ is alkylene of at least 2, preferably 2 to 5 carbon atoms. Preferably, each of the $R^1$ through $R^4$ independently is H or straight, branched, or cyclic hydrocarbyl such as alkyl of 1 to 10 carbon atoms, preferably 1 to 3 carbon atoms. More preferably, each of $R^1$ through $R^4$ is H.

A preferred spacing group for use in the first component is a C3 spacing that has the FORMULA III

FORMULA III wherein each R is independently H, a monovalent moiety or co-member of a structure with one or more other R groups or N-substituents that are generally inert to reaction with amine groups under the transamination conditions to be used. Each R independently may be linear, branched, cyclic, substituted, unsubstituted, aliphatic, aromatic, saturated, and/or unsaturated. In some embodiments, any R independently may be an oligomeric and/or polymeric chain grafted or otherwise bonded to the spacer atoms. Exemplary grafts may be, for instance, polyurethane, poly(meth)acrylic, polyester, polyolefin, polyether, fluorinated, combinations of these, and the like. In other exemplary embodiments, each R is independently H, a hydrocarbyl of 1 to 20 carbon atoms, a group containing a hetero atom, such as an ether moiety or an amine moiety of the formula —$NR^1R^2$, wherein $R^1$ and $R^2$ is H or a hydrocarbyl, including one or more hetero atoms and from 1 to 50 carbon atoms; substituted or unsubstituted aryl, or the like. More preferably, each R is independently H, a hydrocarbyl of 1 to 4 carbon atoms, or an ether of 1 to 4 carbon atoms. Most preferably, each R is H or methyl.

Examples of polyamines useful as the first component include 1,3-diaminopropane (1,3-DAP), 1,3-pentanediamine; 1,3-butanediamine; 2,2-dimethyl-1,3-propanediamine; 2,2-diethyl-1,3-propanediamine; 1,3-diamino-2-phenylpropane; 2-(aminomethyl)-2-methyl-1,3-propanediamine; combinations of these, and the like. 1,3-DAP is most preferred. The second nitrogen-containing reactant preferably has at least two non-tertiary amine groups, separated from one another by a ternary or greater carbon group.

In an aspect of the invention, a second nitrogen-containing compound may be employed in the reaction mixture. The second nitrogen-containing compound preferably comprises (i) at least two non-tertiary amine groups separated from one another by a ternary or greater carbon atom spacing (C3 or greater spacing), (ii) at least two nitrile functionalities separated by at least one carbon atom (C1 spacing), (iii) at least one nitrile functionality and one non-tertiary amine functionality separated from one another by a binary or greater carbon atom spacing (C2 or greater spacing), or (iv) combinations thereof.

Second nitrogen-containing compounds that comprise at least two non-tertiary amine groups separated from one another by a ternary, or greater, carbon atom spacing (C3 or greater spacing) are preferably polyamines represented by FORMULA I.

Examples of polyamines useful as the second nitrogen-containing compound include those identified above as useful as the first nitrogen-containing polyamine compound.

Second nitrogen-containing compounds that comprise either at least two nitrile functionalities separated by at least one carbon atom (C1 spacing), or at least one nitrile functionality and one non-tertiary amine functionality separated from one another by a binary or greater carbon atom spacing (C2 or greater spacing) may be represented by FORMULA II

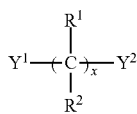

FORMULA II wherein $Y^1$ and $Y^2$ are each CN wherein x is an integer of from 1 to about 10, preferably from 1 to about 5; most preferably 1;

or $Y^1$ is CN and $Y^2$ is independently a non-tertiary amine wherein x is an integer of from 2 to about 10, preferably from 2 to about 5; most preferably 2; and $R^1$ and $R^2$ are as defined above.

Examples of useful nitrogen-containing second compounds of FORMULA II include dinitriles, aminonitriles, and combinations thereof. Specific examples of these compounds include malononitrile, succinonitrile, glutaronitrile, adiponitrile, 2-aminoacetonitrile, 3-aminopropanenitrile, 4-aminobutanenitrile, 2-methylmalononitrile, and 2-methylsuccinonitrile.

In preferred reaction mixture embodiments, the first polyamine component includes at least 1,3 diaminopropane (DAP) having a C3 spacer between amine groups, and the second polyamine component includes any other polyamine component as discussed above.

Transamination of the reactant mixture results in a product mixture that includes many useful polyamine products. These include amine products that are linear, and branched. Polyamine products can be tri-, tetra, or higher in functionality with respect to amine and generally include ternary and greater than ternary spacing between the amine groups.

In the modes of practice in which mixtures of 1,3-DAP and 1,4-diaminobutane are subjected to transamination, exemplary acyclic amine products include triamines: dipropylenetriamine, $N^1$-(3-aminopropyl)butane-1,4-diamine, and $N^1$-(4-aminobutyl)butane-1,4-diamine, tetraamines: $N^1,N^{1'}$-(propane-1,3-diyl)bis(propane-1,3-diamine), $N^1$-(4-aminobutyl)-N4-(3-aminopropyl)butane-1,4-diamine, $N^1$-(3-((3-aminopropyl)amino)propyl)butane-1,4-diamine, $N^1,N^{1'}$-(butane-1,4-diyl)bis(propane-1,3-diamine), $N^1,N^{1'}$-(propane-1,3-diyl)bis(butane-1,4-diamine), and $N^1,N^{1'}$-(butane-1,4-diyl)bis(butane-1,4-diamine); and several pentamine congeners.

Advantageously, transamination of mixtures of polyamines with ternary and greater than ternary spacing may be carried out to provide significant quantities of acyclic products in the product mixture. The acyclic products include linear and branched amines. They may also include some minor amounts (i.e., less than about 30 mole percent) of cyclic. However, the present invention encourages the formation of the linear products so that the formation of the cyclic and branched products is minimized.

The present invention can be practiced to provide polyamine mixtures with significant higher molecular weight content. This is very advantageous as there are many uses where higher molecular weight polyamines in the product mix is strongly desired. Amine mixtures containing these higher molecular weight materials, especially linear materials, have shown a greater adhesion ability and are especially useful as a sizing in paper manufacturing, water treatment conditioning, as a plating bath agent, and as a dispersing agent to name a few. Other exemplary uses for product mixtures of the invention include other polymer curing, hydrocarbon purification, corrosion inhibitors, catalysts, surface activation, asphalt compositions, mineral processing aids, fabric softeners, textile additives, surfactants, and catalysts.

While polyamines having binary spacing, may be employed in a polyamine mixture, their inclusion is not preferred. Transamination of polyamines to produce cyclic polyamine-containing products is disclosed in Applicant's co-pending application filed on Nov. 20, 2012, and titled TRANSAMINATION OF NITROGEN-CONTAINING COMPOUNDS TO MAKE CYCLIC AND CYCLIC/ACYCLIC POLYAMINE MIXTURES, U.S. Ser. No. 61/412,026, and published as WO 2012/064483, on May 18, 2012.

By changing the molar content of the reactant mixture as described above, product mixtures with a customized composition suiting a desired end use may be obtained. Thus, information can be obtained that is indicative of the product composition that results, desirably for a given set of transamination conditions, as a function of the molar content of the reactant(s) with ternary spacing over a suitable molar content. Using this information, transamination can be practiced using a molar content effective to provide a desired product composition. Molar content can be selected that favors the formation of various acyclic congener products.

Adjustment of other reaction conditions also helps customize the product mixture. Examples of other reaction conditions that can be used to customize product compositions include the nature of the catalyst, the concentration of catalyst on its carrier in the case of heterogeneous catalysts, the physical form of the catalyst, the pressure of the reaction, the concentration of $H_2$ during the reaction, conversion, temperature, combinations of these, and/or the like.

The product mixture resulting from transamination can be used as is, packaged stored, or modified as desired depending upon the desired end use. In one mode of practice, the product mixture may include amine products with a range of volatilities. If a limited VOC specification is applicable, more volatile components can be removed before the remainder is used, stored, or otherwise handled. If a limited viscosity specification is applicable, more viscous components can be obtained by refining the more volatile (less viscous) components before the remainder is used, stored, or otherwise handled. Components that are removed, and even some by-products, have commercial value and may have many uses. These include being recycled as a feed for the transamination reaction, refined to recover some of the product(s) in more pure form, used as reactants in other reactions, used as is or with any desired modification as products such as epoxy curing agents, combinations of these, and the like. Different components of the product mixture may have different uses, and so the product mixture can be separated into these components based upon the desired end use.

Transamination may be carried out in a variety of ways. In accordance with a preferred mode of practice, the reactants are combined and caused to react in a suitable reactor volume in the presence of a suitable catalyst under temperature and pressure conditions effective to cause the transamination reaction.

Under the reaction conditions, the dinitrile can react with any amine to provide an intermediate which on hydrogenation loses ammonia to give the new polyamine. Alternatively, the dinitrile may be partially hydrogenated to the imine or the diamine or to a mixture of the two, which can then react similarly to other amines.

The methods of the invention can be practiced in any suitable reactor. These include batch reactors, continuous fixed bed reactors, slurry bed reactors, fluidized bed reactors, catalytic distillation reactors, combinations of these, and the like.

The catalyst material employed in the present invention comprises hydrogenation/dehydrogenation catalysts. Useful catalysts are those based upon nickel (such as Raney nickel and Urushibara nickel), rhenium, cobalt, copper, and mixtures thereof. Particularly useful catalysts comprise nickel/rhenium and nickel/cobalt. A most preferred catalyst comprises nickel (Ni) and rhenium (Re). The weight ratio of nickel to rhenium may vary over a wide range. For instance, the weight ratio of nickel to rhenium may be in the range from about 1:1000 to 1000:1, preferably 1:100 to 100:1, more preferably 1:50 to 50:1. Even more desirably, the weight ratio of nickel to rhenium is within these ranges with the proviso that the weight ratio is also greater than 1:1. In illustrative embodiments, using a weight ratio from about 3:1 to 10:1 would be suitable. In preferred embodiments in which a heterogeneous catalyst incorporates nickel and rhenium, a useful support are alumina-silica particles. Such catalysts and methods of making such heterogeneous catalysts on such supports are further described in U.S. Pat. No. 6,534,441. Such catalysts are also further described in Assignee's co-pending U.S. Published Patent Application 2010/0137642, published Jun. 30, 2010, titled "LOW METAL LOADED, ALUMINA SUPPORTED, CATALYST COMPOSITIONS AND AMINATION PROCESS" by Stephen W. King et al Additional suitable catalysts are also described in Assignee's co-pending U.S. Published Patent Application 2010/0087682, published Apr. 8, 2010, titled "LOW METAL CATALYST COMPOSITIONS INCLUDING ACIDIC MIXED METAL OXIDE AS SUPPORT" by Stephen W. King et al.

The catalysts can be heterogeneous, homogeneous, or a combination of these may be used. Heterogeneous catalysts are preferred. Often, heterogeneous catalysts comprise one or more catalytic materials supported upon a suitable substrate. The substrate may be used in various shapes or combinations such as, for example, powder, particle, pellet, granule, extrudate, fiber, shell, honeycomb, plate, or the like. The particles can be regular in shape, irregular, dendritic, dendrite-free, or the like. Preferred supports are particulate in nature or powders.

Particulate support may have a so-called guest/host structure, which may be prepared by adsorbing or adhering fine (less than 100 micrometers, preferably less than 50 micrometers and most preferably less than 10 micrometer in size) nanoporous particles on coarser (greater than 30 mesh) particles. The smaller particles are referred to as guests, while the large particles supporting them are referred to as hosts. This small-particle-supported-on-a-larger-particle composite structure provides very high total exterior surface area while retaining the desirable gas passing characteristics, i.e., low pressure drop, of a coarser particle. In addition, by using smaller particles in constructing these composite particles, inexpensive, coarser particles can be used. Thus, very inexpensive, highly active catalyst particles can be prepared since the bulk of the volume of a catalyst bed may be taken up by the inexpensive, underlying, coarser particles.

The catalytically active material can be incorporated into or onto the guest and/or host particles. Often, the catalytically active material is incorporated mainly onto the guest material before or after the guest/host composite is formed. Guest/host structures and methods of making these are further described in U.S. Publication No. 2005-0095189 A1.

Preferably, the catalyst and/or the supported catalyst composition is calcined and reduced prior to use. Generally, calcining can occur in air or an inert atmosphere such as one based upon nitrogen, argon, carbon dioxide, combinations of these, and the like. Calcining can occur at a variety of elevated temperatures, such as a temperature up to about 1000° C., preferably about 200° C. to about 800° C. Reduction with hydrogen or a mixture of hydrogen and an inert (e.g., nitrogen) can occur at a variety of elevated temperatures, such as a temperature up to about 1000° C. preferably about 250-500° C.

A wide variety of materials may serve as suitable supports in the practice of the present invention. Representative examples include carbonaceous materials, silicaceous materials (such as silica), metal compounds such as metal oxides, combinations of these, and the like. Representative metal oxides include oxides of one or more of magnesium, aluminum, titanium, vanadium, chromium, manganese, iron, cobalt, nickel, copper, zinc, gallium, germanium, strontium, yttrium, zirconium, niobium, molybdenum, technetium, ruthenium, rhodium, palladium, silver, cadmium, indium, iron, tin, antimony, barium, lanthanum, hafnium, thallium, tungsten, rhenium, osmium, iridium, and platinum.

Examples of carbonaceous substances include activated carbon and graphite. Suitable activated carbon particles may be derived from a wide variety of source(s) including coal, coconut, peat, any activated carbon(s) from any source(s), combinations of at least two of these, and/or the like.

Catalytically active material may be incorporated into heterogeneous catalyst systems in a variety of ways. In some instances, a catalyst precursor is first provided on the support, and then the precursor can be converted into the catalyst itself afterward. Exemplary procedures are well known in the industry and include solution impregnation, precipitation, vapor deposition such as by physical or chemical vapor deposition techniques, and the like.

The amount of catalyst used in forming a high molecular weight polyamine using transamination is any amount which is effective in producing the desired acyclic polyamine. For batch conditions, the quantity of catalyst may be in the range from about 0.1 to about 20 weight percent, preferably 1 to 15 weight percent, of catalyst per 100 parts by weight of reactant(s) to form the desired triamine. In a continuous process, a typical strategy might involve causing a flow of reactants to contact a bed of heterogeneous catalyst particles. In such a case, the space velocity (usually expressed in units of gmol/(kg catalyst/hr) can be adjusted to balance factors such as production and selectivity.

When calculating the weight percent of catalyst for batch or continuous processes, only the actual amount of active catalytic substance is used to determine the weight percent of catalyst. For instance, in an exemplary embodiment, 100 parts by weight of heterogeneous catalyst particles might be used to treat a mixture containing 91 parts by weight of 1,3-DAP and 9 parts by weight of 1,4 diaminobutane. Other amines may or may not be present in the mix. The total amount of reactants is 100 parts by weight. The heterogeneous catalyst particles might include 5 part by weight of Ni and 1 part by weight of Re as metals for a total of 6 parts by weight of catalyst. In this case, the batch reactor would include 6 parts by weight of the catalyst per 100 parts by weight of the reactants. For purposes of the present invention, if the catalyst is present as a molecule such as an oxide or the like, only the weight of the active metal catalyst constituent is used to determine the weight percent.

The reaction mixture for transamination can be contacted with catalyst at any suitable temperature(s) that produce the desired acyclic polyamine. Typically, the temperature is maintained below about 350° C., preferably below 300° C. Preferred temperatures are in the range from about 130° C. to about 200° C. for transamination. Below the preferred temperature ranges, the conversion to acyclic polyamine may be too slow to be practical for commercial scale production. Above the preferred temperature ranges, selectivity may be reduced to an undue degree, increasing the yield of by-products. In some instances, such by-products may have commercial value and be desirable as a consequence. In other instances, by-products constitute impurities as a practical matter.

Similarly, the reaction mixture for transamination can be contacted with catalyst at any suitable pressure(s) that promotes the reaction to produce the desired high molecular weight polyamine. Preferably, the pressure is sufficient to maintain the reactor contents in a liquid state as the reaction proceeds. In many instances, the pressure will vary as the reaction proceeds. For instance, ammonia is a by-product of a typical transamination process. The production of ammonia causes the pressure generally to increase as the reaction proceeds in pressure sealed reactors. Ammonia and/or other pressure-increasing products can be removed from the reactor in order to keep the pressure below a desired threshold. Typically, the pressure is at least about 500 psi, preferably at least about 1000 psi, and preferably less than about 1500 psi. Within these guidelines, the pressure is typically in the range from about 100 psi to about 1500 psi, preferably about 200 psi to about 1500 psi, more preferably about 300 psi to about 1000 psi. For transamination, pressures in the range of about 400 psi to about 1000 psi are preferred.

In many embodiments, the amine mixture used as a starting reaction material for transamination will be in liquid form such that no additional solvent is needed. Indeed, in many instances it may be preferred to carry out the desired reaction in the absence of solvent. However, one or more solvents may be used if desired. A variety of solvents or combinations of solvents may be used. Desirably, the solvent is not unduly reactive with the higher amine reactant(s) or the resultant polyamine product(s) and does not unduly decompose under the reaction conditions. Some examples of solvents that could be used include saturated hydrocarbons such as pentane, hexane, octane, nonane, decane, or the like; aromatic hydrocarbons such as toluene, benzene, xylene, ether, combinations of these, and the like. Alcohols are desirably avoided, as many of these are capable of reacting with the amine reactants and/or products. If present, the amount of solvent used may vary over a wide range. In a typical instance, the solvent may constitute from about 5 to about 98 weight percent, desirably 10 to 80 weight percent, of the mixture. Optionally when solvent is used, the reaction medium can be diluted to favor intramolecular reactions and, hence, cyclization, relative to intermolecular interactions.

The reactant mixture for transamination optionally may, and preferably does, include hydrogen. When hydrogen is used, the level of hydrogen can be adjusted to favor the formation of linear products while minimizing the amount of hydrogenolysis that can lead to alkyl byproducts (e.g., N-propyl, 1-3-diaminopropane). From 0.1 to about 100 mole percent, desirably about 1 to about 10 mole percent of hydrogen per mole of reactants would be suitable.

The following Assignee co-pending U.S. patent applications describe technology relating to catalysts and/or transamination: U.S. Pat. Pub. No. 2010/0137642; U.S. Pat. Pub. No. 2010/0087682; U.S. Pat. Pub. No. 2010/0087683; U.S. Pat. Pub. No. 2010/0087684; U.S. Pat. Pub. No. 2010/0094007; U.S. Pat. Pub. No. 2010/0094008; and U.S. Pat. Pub. No. 2010/0087681. Each is incorporated herein by reference in its respective entirety for all purposes.

The molecular weight of the amines produced by the methods of the present invention may be controlled by adding a terminator. A terminator is a non-polyamine which will react with the polyamine mixture to form a tertiary amine. So, for example, a terminator compound may be added during transamination to stop the reaction. Useful terminators include secondary amines (e.g., dimethylamine, diethylamine, etc.).

The present invention will now be further described with reference to the following illustrative examples.

Catalyst Preparation

Unless otherwise noted, the catalyst compositions employed were prepared using the following procedure. Precursor salts of the metals (nickel and rhenium) were dissolved in 70-80° C. water to form an impregnation solution. The final volume of the impregnation solution was adjusted to equal the adsorption volume required for the number of times that the support was impregnated, and the quantities of the precursor salts were those calculated to give the metal compositions provided in the Examples. In each case the support was impregnated to incipient wetness by the addition of the appropriate amount of impregnation solution and gently agitated until all the liquid was adsorbed. The sample was then placed in a muffle furnace and calcined in air for one hour at 340° C. or as otherwise specified in the Examples. When the support had cooled, additional impregnations were performed until all of the solution had been added. A calcination step at 340° C. was done after each impregnation.

Those skilled in the art will readily appreciate that impregnation with the impregnation solution can optionally be performed in one, two, four or more incipient wetness applications, as dictated by such variables as the solubility of the precursor salts, the porosity of the support to be impregnated, and the desired weight loading of the metal.

Prior to use, the catalyst compositions were reduced in hydrogen by ramping the temperature at 3° C./minute to 230° C., holding at this temperature for one hour, and then ramping at 3° C./minute to 340° C., and holding for 3 hours, or as otherwise specified in the Examples. The catalyst compositions were allowed to cool under hydrogen to ambient temperature, after which they were stabilized by adding a flowing stream of 1% oxygen in nitrogen until the exotherm ceased. At no time was the exotherm allowed to exceed about 70° C.

Reaction Conditions

The reactions were conducted in a 2 L high-pressure 316SS autoclave (Autoclave Engineers) equipped with a magnetic stirrer, a dip tube for sampling, and a catalyst basket.

The catalyst was charged to the catalyst basket and activated overnight with flowing hydrogen at 180° C. The autoclave was cooled to room temperature, and the liquid reactant(s) charged by pressure, taking care not to admit air. The autoclave was brought to operating pressure with hydrogen, and heated to operating temperature with stirring. Samples were taken hourly via a dip tube and analyzed by GC. Prior to analysis, ammonia (if present) was allowed to evaporate. Gas Chromatography analyses of the product mixtures were done on a DB-5MS, 30 m×0.32 mm ID×1 micron column. Peaks were identified with the aid of GC/mass spec. All GC peaks represent % by weight of the designated product in the mixture.

Example 1

A total of 1000 grams of 1,3-diaminopropane (1,3-DAP), a polyamine with two primary amines with a ternary spacer, was charged to the 2 L high pressure autoclave described above. The reactor was heated from 130-148° C. Samples were obtained starting after 2 hours of reaction time until 6 hours and analyzed as described above. The results are given in Table 1 A predominately linear high molecular weight polyamine product mixture was obtained.

Example 2

A total of 1000 grams of dipropylenetriamine (DPTA), a polyamine with a ternary spacing between a primary and secondary amine, was charged to the 2 L high pressure autoclave described above. The reactor was heated from 133-151° C. Samples were obtained starting after 2 hours of reaction time until 8 hours and analyzed as described above. The results are given in Table 2. A predominately linear high molecular weight polyamine product mixture was obtained.

TABLE 1

1,3-diaminopropane (1,3-DAP) starter
100 grams Ni—Re alumina/silica
1000 grams 1,3-DAP charge
500 PSIG hydrogen

| Sample No. | 1 | 2 | 3 | 4 |
|---|---|---|---|---|
| Time, hrs | 2 | 3.25 | 5 | 6 |
| Temp, ° C. | 130 | 141 | 143 | 148 |
| Press, PSIG | 840 | 880 | 923 | 910 |
| 1,3-DAP Conversion | 38.16 | 65.85 | 81.83 | 88.98 |
| GC Results, Area % | | | | |
| propylamine | 0.04 | 1.20 | 1.26 | 1.28 |
| 1,3 diaminopropane | 61.84 | 34.15 | 18.17 | 11.02 |
| N-propyl-1,3-diaminopropane | 0.33 | 1.00 | 1.29 | 1.43 |
| dipropylenetriamine | 27.98 | 33.45 | 28.95 | 22.71 |
| N-propyl-dipropylenetriamine | 0.08 | 0.47 | 0.81 | 1.05 |
| tripropylenetetramine | 6.93 | 16.69 | 22.01 | 21.72 |
| N-propyl-tripropylenetetramine | 0.02 | 0.21 | 0.44 | 0.67 |
| tetrapropylenepentamine | 1.46 | 6.86 | 12.86 | 15.68 |
| N-propyl-tetrapropylenepentamine | 0.01 | 0.09 | 0.23 | 0.38 |
| pentapropylenehexamine | 0.02 | 0.14 | 6.67 | 10.25 |
| hexapropyleneheptamine | 0.01 | 0.14 | 3.24 | 6.18 |
| heptapropyleneoctamine | 0.00 | 0.08 | 1.36 | 3.56 |
| octapropylenenonamine | | | 0.38 | 1.79 |
| Others | 1.28 | 5.51 | 2.34 | 2.28 |

TABLE 2 dipropylenetriamine (DPTA) starter
100 grams Ni—Re alumina/silica
1000 grams DPTA charge
500 PSIG hydrogen

| Sample No. | 1 | 2 | 3 | 4 | 5 | 6 |
|---|---|---|---|---|---|---|
| Time, hrs | 2 | 3 | 5 | 6 | 7 | 8 |
| Temp, ° C. | 133 | 133 | 145 | 143 | 142 | 151 |
| Press, PSIG | 835 | 820 | 830 | 830 | 834 | 816 |
| DPTA Conversion | 24.67 | 33.88 | 64.23 | 74.12 | 80.92 | 89.21 |
| GC Results, Area % | | | | | | |
| propylamine | 0.04 | 0.05 | 0.12 | 0.16 | 0.18 | 0.40 |
| 1,3 diaminopropane | 0.58 | 0.71 | 1.20 | 1.35 | 1.48 | 1.83 |
| N-propyl-1,3-diaminopropane | 0.01 | 0.01 | 0.04 | 0.06 | 0.09 | 0.23 |
| dipropylenetriamine | 75.33 | 66.12 | 35.77 | 25.88 | 19.08 | 10.79 |
| N-propyl-dipropylenetriamine | 0.35 | 0.45 | 0.75 | 0.85 | 0.97 | 1.28 |
| tripropylenetetramine | 1.59 | 2.14 | 4.50 | 5.44 | 6.26 | 7.34 |
| N-propyl-tripropylenetetramine | 0.01 | 0.01 | 0.06 | 0.09 | 0.15 | 0.40 |
| tetrapropylenepentamine | 17.36 | 22.28 | 30.45 | 29.87 | 28.07 | 22.23 |
| N-propyl-tetrapropylenepentamine | 0.08 | 0.13 | 0.37 | 0.52 | 0.68 | 1.05 |
| pentapropylenehexamine | 0.61 | 1.05 | 4.07 | 5.90 | 7.81 | 10.92 |
| hexapropyleneheptamine | 2.92 | 4.94 | 14.01 | 17.41 | 19.72 | 21.16 |
| heptapropyleneoctamine | 0.15 | 0.32 | 2.33 | 3.89 | 5.60 | 8.93 |
| octapropylenenonamine | 0.45 | 1.01 | 4.42 | 6.16 | 6.83 | 8.42 |
| Others | 0.53 | 0.78 | 1.90 | 2.41 | 3.07 | 5.03 |

Comparative Example

The above procedure was repeated using 800 grams of 1,2-diaminopropane (1,2-DAP), a polyamine with two primary amines and a binary carbon atom spacing. The reactor was heated from 153-157° C. Samples were obtained starting after 5 hours of reaction time until 7 hours and analyzed as described above. The results are given in Table 3. These results demonstrate that high molecular weight polyamines are not made and the resultant product mix is high in cyclic content when 1,2-diaminopropane which has a binary carbon atom spacing is used as the starting material.

TABLE 3

| 1,2-diaminopropane starter | | |
|---|---|---|
| 100 grams Ni—Re alumina/silica | | |
| 800 grams liquid charge | | |
| 400 PSIG hydrogen | | |
| Sample No. | 1 | 2 |
| Time, hrs | 5 | 7 |
| Temp ° C. | 153 | 157 |
| Press, PSIG | 816 | 800 |
| % Conversion | 30.9 | 56.5 |
| GC Results, Area % | | |
| 1,2-diaminopropane | 69.1 | 43.5 |
| 2,6-dimethylpiperazine | 4.6 | 16 |
| 2,5-dimethylpiperazine (trans) | 2.5 | 5.1 |
| 2,5-dimethylpiperazine (cis) | 5.7 | 13.9 |
| mixture of dimethyl substituted triamines | 14.7 | 13.9 |
| Others | 3.3 | 7.7 |

What is claimed is:

1. A method of making a product mixture of linear high molecular weight polyamines having four or more N atoms comprising the steps of:
   (a) providing a reaction composition comprising one or more nitrogen-containing compounds comprising a first component that has at least two non-tertiary amine groups separated from one another by at least a ternary or higher carbon atom spacing (C3 or greater spacing) and, optionally, a second component that has at least two nitrogen containing groups separated from one another by a binary or higher carbon atom spacing (C2 or higher spacing); wherein the molar content of the first component is at least 95% of the reaction composition; and
   (b) subjecting the reaction composition to a transamination reaction in the presence of a hydrogenation/dehydrogenation catalyst to obtain the mixture of linear high molecular weight polyamines having four or more N atoms.

2. The method of claim 1, wherein the second component comprises a nitrogen-containing compound having (i) at least two non-tertiary amine groups separated from one another by a ternary or greater carbon atom spacing (C3 or greater spacing), or (ii) at least one nitrile functionality and one non-tertiary amine functionality separated from one another by a binary or greater carbon atom spacing (C2 or greater spacing), or(iii) combinations thereof.

3. The method of claim 1, wherein the first component comprises a polyamine that has the formula

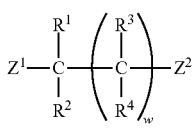

FORMULA I wherein $Z^1$ and $Z^2$ are independently primary or secondary amines;
R1, $R^2$, $R^3$ and $R^4$ are independently H or substituted or unsubstituted hydrocarbyl; and
w is an integer of 2 or more.

4. The method of claim 1 wherein the second component comprises a nitrile compound having the formula

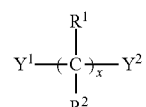

FORMULA II wherein
$Y^1$ is CN and $Y^2$ is independently a non-tertiary amine wherein x is an integer of from 2 to about 10; and
$R^1$ and $R^2$ are independently H or substituted or unsubstituted hydrocarbyl.

5. The method of claim 1, wherein the first component has a ternary carbon atom spacing having the formula

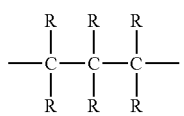

FORMULA III wherein each R is independently H, a monovalent moiety or co-member of a structure with one or more other R groups or N-substituents that are inert to reaction with amine groups under the transamination, and wherein each R independently may be linear, branched, cyclic, substituted, unsubstituted, aliphatic, aromatic, saturated, and/or unsaturated.

6. The method of claim 3, wherein each R is H.

7. A method of making a mixture of congeners of high molecular weight polyamines having 4 or more N atoms, comprising the steps of: providing a reaction mixture comprising first component comprising at least one organic, nitrogen-containing compound that contains at least two non-tertiary amines separated from one another by at least a ternary or greater carbon atom spacing; and a second component comprising a nitrogen-containing compound that contains at least two nitrogen-containing functional groups separated from one another by a second carbon atom spacing, wherein molar content of the first component is at least 95% of the reaction mixture, and subjecting the reaction mixture to a transamination reaction in the presence of a hydrogenation/dehydrogenation catalyst to obtain a product mixture comprising the mixture of the congeners of the higher molecular weight polyamines.

8. The method of claim 1, wherein the polyamine product comprises less than about 1 weight percent cyclic polyamine.

9. The method of claim 1, wherein the catalyst comprises a Ni/Re catalyst.

10. The method of claim 1, wherein polyamine mixture comprises a polyamine product that has a molecular weight of at least 130.

11. The method of claim 1, wherein the reaction mixture comprises from about 0.1 to about 100 moles of hydrogen per mole of reactants.

12. The method of claim 4, wherein each R is H.

13. The method of claim 5, wherein each R is H.

* * * * *